(12) United States Patent
Schaeffer-Korbylo et al.

(10) Patent No.: US 9,561,168 B2
(45) Date of Patent: Feb. 7, 2017

(54) ORAL CARE COMPOSITIONS

(75) Inventors: Lyndsay Schaeffer-Korbylo, Flemington, NJ (US); Christine Cuiule, Mount Laurel, NJ (US); Laurence Du-Thumm, Princeton, NJ (US)

(73) Assignee: Colgate-Palmolive Company, New York, NY (US)

(*) Notice: Subject to any disclaimer, the term of this patent is extended or adjusted under 35 U.S.C. 154(b) by 183 days.

(21) Appl. No.: 14/364,877

(22) PCT Filed: Dec. 15, 2011

(86) PCT No.: PCT/US2011/065129
§ 371 (c)(1),
(2), (4) Date: Jun. 12, 2014

(87) PCT Pub. No.: WO2013/089735
PCT Pub. Date: Jun. 20, 2013

(65) Prior Publication Data
US 2014/0308217 A1    Oct. 16, 2014

(51) Int. Cl.
*A61K 8/64* (2006.01)
*A61K 8/58* (2006.01)
*A61K 8/19* (2006.01)
*A61Q 11/00* (2006.01)
*A61K 8/88* (2006.01)

(52) U.S. Cl.
CPC . *A61K 8/64* (2013.01); *A61K 8/19* (2013.01); *A61K 8/58* (2013.01); *A61K 8/88* (2013.01); *A61Q 11/00* (2013.01)

(58) Field of Classification Search
USPC .......................................................... 424/49
See application file for complete search history.

(56) References Cited

U.S. PATENT DOCUMENTS

| | | |
|---|---|---|
| 3,535,421 A | 10/1970 | Briner et al. |
| 3,538,230 A | 11/1970 | Pader et al. |
| 3,678,154 A | 7/1972 | Widder et al. |
| 3,696,191 A | 10/1972 | Weeks |
| 3,862,307 A | 1/1975 | Di Giulio |
| 3,937,807 A | 2/1976 | Haefele |
| 3,959,458 A | 5/1976 | Agricola et al. |
| 3,991,177 A | 11/1976 | Vidra et al. |
| 4,051,234 A | 9/1977 | Gieske et al. |
| 4,058,595 A | 11/1977 | Colodney |
| 4,154,815 A | 5/1979 | Pader |
| 4,340,583 A | 7/1982 | Wason |
| 4,355,022 A | 10/1982 | Rabussay |
| 4,842,847 A | 6/1989 | Amjad |
| 4,866,161 A | 9/1989 | Sikes et al. |
| 4,885,155 A | 12/1989 | Parran, Jr. et al. |
| 4,992,420 A | 2/1991 | Neeser |
| 5,000,939 A | 3/1991 | Dring et al. |
| 5,004,597 A | 4/1991 | Majeti et al. |
| 5,188,821 A | 2/1993 | Gaffar et al. |
| 5,192,531 A | 3/1993 | Gaffar et al. |
| 5,286,480 A | 2/1994 | Boggs et al. |
| 7,973,006 B2 | 7/2011 | Otto et al. |
| 2008/0226565 A1 | 9/2008 | Huybrechts |
| 2008/0241275 A1 | 10/2008 | Perl et al. |
| 2009/0082443 A1 | 3/2009 | Otto et al. |
| 2009/0202658 A1 | 8/2009 | Cuero |
| 2011/0038809 A1* | 2/2011 | Perl .................. A23K 1/175 424/49 |

FOREIGN PATENT DOCUMENTS

| | | |
|---|---|---|
| CN | 101374511 | 2/2009 |
| EP | 1832182 | 12/2007 |
| JP | 2004107310 | 4/2004 |
| JP | 2007008843 | 1/2007 |
| WO | WO2005068645 | 7/2005 |
| WO | WO2006117029 | 11/2006 |
| WO | WO2007053581 | 5/2007 |

OTHER PUBLICATIONS

Corresponding Eurpoean Offtce Action dated Nov. 6, 2015.
Database WPI, Week 200718, Thomson Scientific, London, GB: AN 2007-180895 & JP 2007 008843 A (Lion Corp) Jan. 18, 2007 (Jan. 2007).
International Search Report and the Written Opinion issued in International Application PCT/US2011/65129 mailed Nov. 2, 2012. WO.
Written Opinion of the International Preliminary Examining Authority issued in International Application PCT/US2011/65129 mailed Dec. 4, 2012. WO.

\* cited by examiner

*Primary Examiner* — Walter Webb

(57) ABSTRACT

Described herein are oral care compositions comprising (i) an orally acceptable gallium salt and (ii) a basic amino acid polymer, in amounts effective to disrupt biofilm; and methods of making and using the same.

12 Claims, No Drawings

ORAL CARE COMPOSITIONS

BACKGROUND

Although many antibacterial agents are tested on free-floating, planktonic cultures of bacteria, these organisms rarely exist this way in nature. More commonly, bacteria are found in complex communities called biofilms. This is especially true in the oral cavity where up to 700 species of bacteria form a complicated mixed species biofilm commonly referred to as dental plaque. Dental plaque may lead to a variety of undesirable conditions, including erosion of the enamel, dental hypersensitivity, halitosis, tooth decay, caries and gingivitis. Relative to free living bacteria, bacteria found in biofilms differ in their metabolic rates, nutrient access and requirements and susceptibility to antimicrobial agents. Agents that are active against bacteria in culture may be relatively ineffective against bacteria in plaque, absent some mechanism to disrupt the biofilm.

Gallium is a transition metal generally found in gallium (III) salt form. Due to its similarity in size and charge to iron, the body handles $Ga^{3+}$ in many ways as though it were iron, and thus it is bound (and concentrates) in areas of inflammation, such as infection, and also areas of rapid cell division. Gallium salts have thus been used in a number of biomedical applications to target iron-based mechanisms, e.g., as a carrier of radiation for nuclear medicine, to treat pain associated with arthritis, and to treat hypercalcemia sometimes associated with cancer treatment. Gallium is also known to be an antibacterial agent, as it is readily taken up by the iron-scavenging mechanisms of bacterial cells. Most bacteria require iron for survival, but as they often exist in iron-poor environments, they have developed a variety of mechanisms for iron scavenging. When gallium is taken up in place of iron, it cannot be used in the same manner, and it effectively poisons the bacterial cells.

ε-Polylysine is a polymer composed of l-lysine molecules with an amide linkage between the ε-amino and α-carboxyl groups. This compound is a naturally occurring product of microbial fermentation and has been used as a food preservative.

There is a need for safe and effective oral care products which are not only effective against bacteria in a free-floating culture, but are capable of disrupting the biofilm forming dental plaque, and rendering the bacteria susceptible to removal and destruction.

SUMMARY

We have investigated gallium and ε-polylysine as potential antibacterial, antibiofilm agents for use in oral care products. While each of these agents individually have relatively poor activity against multispecies biofilms such as are found in the oral cavity, we have surprisingly found that in combination, they greatly inhibit multispecies biofilm formation.

Accordingly, the invention provides oral care compositions comprising effective amounts of (i) an orally acceptable gallium salt and (ii) a basic amino acid polymer, e.g., ε-polylysine, together with methods of making and using such compositions as antibacterial and antiplaque agents to reduce and eliminate bacterial biofilms in the oral cavity.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

The invention thus provides, in a first embodiment, an oral care composition (Composition 1) comprising effective amounts, e.g. biofilm-disruptive concentrations, of (i) an orally acceptable gallium salt and (ii) a basic amino acid polymer; for example, 1.1. Composition 1 wherein the orally acceptable gallium salt is a gallium (III) salt;

1.2. Composition 1.1 wherein the orally acceptable gallium salt comprises gallium nitrate, gallium citrate, gallium maltolate, or mixtures thereof;

1.3. Composition 1.2 wherein the orally acceptable gallium salt comprises gallium nitrate;

1.4. Any of the foregoing compositions wherein the basic amino acid polymer is selected from comprises ε-polylysine, polyarginine, polyhistidine, polycitrullene, and combinations thereof;

1.5. Any of the foregoing compositions wherein the basic amino acid polymer comprises ε-polylysine;

1.6. Any of the foregoing compositions wherein the amount of orally acceptable gallium salt is from 0.001 to 5%, e.g., 0.01%-0.5%;

1.7. Any of the foregoing compositions wherein the amount of orally acceptable gallium salt is about 0.01-0.05%;

1.8. Any of the foregoing compositions wherein the amount of orally acceptable gallium salt is about 0.1 to 0.5%;

1.9. Any of the foregoing compositions wherein the amount of basic amino acid polymer is from 0.001 to 5%, e.g., 0.01%-0.5%;

1.10. Any of the foregoing compositions wherein the amount of basic amino acid polymer is about 0.01-0.05%;

1.11. Any of the foregoing compositions wherein the amount of basic amino acid polymer is about 0.1 to 0.5%;

1.12. Any of the foregoing compositions further comprising an effective amount of fluoride, e.g., wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof;

1.13. Any of the foregoing compositions comprising l-arginine in free or orally acceptable salt form;

1.14. Any of the foregoing compositions comprising buffering agents, e.g., sodium phosphate buffer (e.g., sodium phosphate monobasic and disodium phosphate)

1.15. Any of the foregoing compositions comprising a humectant, e.g., selected from glycerin, sorbitol, propylene glycol, polyethylene glycol, xylitol, and mixtures thereof;

1.16. Any of the preceding compositions further comprising an abrasive or particulate;

1.17. The immediately preceding composition wherein the adhesive or particulate is selected from sodium bicarbonate, calcium phosphate (e.g., dicalcium phosphate dihydrate), calcium sulfate, precipitated calcium carbonate, silica (e.g., hydrated silica), iron oxide, aluminum oxide, perlite, plastic particles, e.g., polyethylene, and combinations thereof;

1.18. Any of the preceding compositions comprising an abrasive in an amount of about 15 wt. % to about 70 wt. % of the total composition weight;

1.19. Any of the preceding compositions comprising one or more surfactants, e.g., selected from anionic, cationic, zwitterionic, and nonionic surfactants, and mixtures thereof, e.g., comprising an anionic surfactant, e.g., a surfactant selected from sodium lauryl sulfate, sodium ether lauryl sulfate, and mixtures thereof, e.g. in an amount of from about 0.3% to about 4.5% by weight;

1.20. Any of the preceding compositions further comprising at least one polymer in addition to the basic amino acid polymer, e.g., selected from polyethylene glycols, polyvinylmethyl ether maleic acid copolymers, polysaccharides (e.g., cellulose derivatives, for example carboxymethyl cellulose, or polysaccharide gums, for example xanthan gum or carrageenan gum), and combinations thereof;

1.21. Any of the preceding compositions comprising gum strips or fragments;

1.22. Any of the preceding compositions further comprising flavoring, fragrance and/or coloring;

1.23. Any of the preceding compositions further comprising water;

1.24. Any of the foregoing compositions comprising one or more antibacterial agents in addition to the gallium salt and the basic amino acid polymer, for example comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride;

1.25. Any of the preceding compositions further comprising a whitening agent, e.g., a selected from the group consisting of peroxides, metal chlorites, perborates, percarbonates, peroxyacids, hypochlorites, and combinations thereof;

1.26. Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate);

1.27. Any of the preceding compositions further comprising an agent that interferes with or prevents bacterial attachment, e.g., solbrol or chitosan;

1.28. Any of the preceding compositions further comprising a source of calcium and phosphate selected from (i) calcium-glass complexes, e.g., calcium sodium phosphosilicates, and (ii) calcium-protein complexes, e.g., casein phosphopeptide-amorphous calcium phosphate;

1.29. Any of the preceding compositions further comprising a soluble calcium salt, e.g., selected from calcium sulfate, calcium chloride, calcium nitrate, calcium acetate, calcium lactate, and combinations thereof;

1.30. Any of the preceding compositions further comprising a physiologically acceptable potassium salt, e.g., potassium nitrate or potassium chloride, in an amount effective to reduce dentinal sensitivity;

1.31. Any of the preceding compositions further comprising a breath freshener, fragrance or flavoring;

1.32. Any of the preceding compositions effective upon application to the oral cavity, e.g., with brushing, to (i) inhibit microbial biofilm formation in the oral cavity, (ii) to reduce plaque accumulation, (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; and/or (xv) promote whole body health, including cardiovascular health, e.g., by reducing potential for systemic infection via the oral tissues;

1.33. A composition obtained or obtainable by combining the ingredients as set forth in any of the preceding compositions;

1.34. Any of the preceding compositions in a form selected from mouthrinse, toothpaste, tooth gel, tooth powder, non-abrasive gel, mousse, foam, mouth spray, lozenge, oral tablet, dental implement, and pet care product;

1.35. Any of the preceding compositions further comprising effective amounts of additional agents selected from fluoride, l-arginine in free or orally acceptable salt form, antibacterial agents in addition to the gallium salt and the basic amino acid polymer, anti-inflammatory compounds, and whitening agents;

1.36. Any of the preceding compositions wherein the composition is a toothpaste or mouthwash optionally further comprising one or more of one or more of water, abrasives, surfactants, foaming agents, vitamins, polymers, enzymes, humectants, thickeners, antimicrobial agents, preservatives, flavorings, colorings and/or combinations thereof;

1.37. Any of the preceding compositions wherein the composition is toothpaste;

1.38. Any of the preceding compositions 1-1.37 wherein the composition is a mouthwash;

The invention further provides methods to (i) inhibit microbial biofilm formation in the oral cavity, (ii) to reduce plaque accumulation, (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; and/or (xv) promote systemic health, including cardiovascular health, e.g., by reducing potential for systemic infection via the oral tissues; comprising applying to the oral cavity an effective amount of a composition comprising of (i) an orally acceptable gallium salt and (ii) a basic amino acid polymer, e.g., any of Composition 1, et seq.

The invention further provides the use of (i) an orally acceptable gallium salt and (ii) a basic amino acid polymer, in the manufacture of an oral care composition, e.g., any of Composition 1, et seq., e.g., for use in any of the methods as described in the preceding paragraph, as well as methods of manufacturing an oral care composition, e.g., Composition 1, et seq., comprising combining (i) an orally acceptable gallium salt and (ii) a basic amino acid polymer together with an orally acceptable carrier.

Salt Forms:

The compositions of the invention are intended for topical use in the mouth, thus salts for use in the present invention should be orally acceptable, that is, safe for topical use in the mouth, in the amounts and concentrations provided. Suitable salts include salts known in the art to be pharmaceutically acceptable salts, which are generally considered to be orally acceptable for this purpose in the amounts and concentrations provided. Gallium is generally found in the gallium (III) oxidation state, and is thus capable of forming salts with pharmaceutically acceptable inorganic or organic acids. Preferably, the gallium (III) salt is sufficiently soluble to provide an effective level of $Ga^{3+}$ ions upon use. Preferred gallium salts include orally acceptable salts of gallium(III), for example gallium nitrate, gallium citrate and gallium maltolate.

Active Agents:

The effective concentration of the active ingredients used herein will depend on the particular agent and the delivery system used. It is understood that a toothpaste for example will typically be diluted with water upon use, while a mouth rinse typically will not be. Thus, an effective concentration of active in a toothpaste will ordinarily be 5-15× higher than required for a mouth rinse. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. Effective concentrations of gallium salts for use in the instant invention are thus, e.g., from 0.001 to 5%, e.g., about 0.01-0.05% for a mouth rinse and about 0.1 to 0.5% for a toothpaste. Effective concentrations of basic amino acid polymer for use in the instant invention are similar, e.g., from 0.001 to 5%, e.g., about 0.01-0.05% for a mouth rinse and about 0.1 to 0.5% for a toothpaste. Other actives are provided in effective amounts. Arginine, where present, may be present at levels from, e.g., about 0.1 to about 20 wt % (expressed as weight of free base), e.g., about 0.1 to about 3 wt % for a mouthrinse, about 1 to about 10 wt % for a consumer toothpaste or about 7 to about 20 wt % for a professional or prescription treatment product. Fluoride where present may be present at levels of, e.g., about 25 to about 25,000 ppm, for example about 25 to about 250 ppm for a mouthrinse, about 750 to about 2,000 ppm for a consumer toothpaste, or about 2,000 to about 25,000 ppm for a professional or prescription treatment product. Levels of antibacterial agents in addition to the gallium salt and basic amino acid polymer will vary similarly, with levels used in toothpaste being e.g., about 5 to about 15 times greater than used in mouthrinse. For example, a triclosan mouthrinse may contain, e.g., about 0.03 wt % triclosan while a triclosan toothpaste may contain about 0.3 wt % triclosan.

Basic Amino Acids:

Basic amino acids are preferably those basic amino acids capable of forming charged polymers. For example, ε-polylysine is preferred to α-polylysine because the free amino groups in ε-polylysine have a positive charge. Polyarginine, polyhistidine and polycitrullene are also suitable as their nitrogenous side chains are positively charged.

Fluoride Ion Source:

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition of the invention may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A mouthwash, for example, would typically have about 100 to about 250 ppm fluoride. A toothpaste for general consumer use would typically have about 1000 to about 1500 ppm, with pediatric toothpaste having somewhat less. A dentifrice or coating for professional application could have as much as about 5,000 or even about 25,000 ppm fluoride. Fluoride ion sources may be added to the compositions of the invention at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counter ion in the salt.

Abrasives:

The compositions of the invention, e.g. Composition 1 et seq. may comprise a calcium phosphate abrasive, e.g., tricalcium phosphate $(Ca_3(PO_4)_2)$, hydroxyapatite $(Ca_{10}(PO_4)_6(OH)_2)$, or dicalcium phosphate dihydrate $(CaHPO_4.2H_2O$, also sometimes referred to herein as DiCal)

or calcium pyrophosphate. The compositions may include one or more additional abrasives, for example silica abrasives such as precipitated silicas having a mean particle size of up to about 20 microns, such as Zeodent 115®, marketed by J. M. Huber. Other useful abrasives also include sodium metaphosphate, potassium metaphosphate, aluminum silicate, calcined alumina, bentonite or other siliceous materials, or combinations thereof. The silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio, both incorporated herein by reference. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, incorporated herein by reference. In certain embodiments, abrasive materials useful in the practice of the oral care compositions in accordance with the invention include silica gels and precipitated amorphous silica having an oil absorption value of less than about 100 cc/100 g silica and in the range of about 45 cc/100 g to about 70 cc/100 g silica. Oil absorption values are measured using the ASIA Rub-Out Method D281. In certain embodiments, the silicas are colloidal particles having an average particle size of about 3 microns to about 12 microns, and about 5 to about 10 microns. Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive useful in the practice of the present invention. The abrasive is present in the oral care composition of the present invention at a concentration of about 10 to about 60% by weight, in other embodiment about 20 to about 45% by weight, and in another embodiment about 30 to about 50% by weight.

Agents to Increase the Amount of Foaming:

The oral care compositions of the invention also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions of the present invention. The dosage of foaming agent in the oral care composition (i.e., a single dose) is about 0.01 to about 0.9% by weight, about 0.05 to about 0.5% by weight, and in another embodiment about 0.1 to about 0.2% by weight.

Surfactants:

The compositions useful in the invention may contain anionic surfactants, for example
  i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate,
  ii. higher alkyl sulfates, such as sodium lauryl sulfate,
  iii. higher alkyl-ether sulfates, e.g., of formula $CH_3(CH_2)mCH_2(OCH_2CH_2)nOSO_3X$, wherein m is 6-16, e.g., 10, n is 1-6, e.g., 2, 3 or 4, and X is Na or K, for example sodium laureth-2 sulfate ($CH_3(CH_2)10CH_2(OCH_2CH_2)2OSO_3Na$).
  iv. higher alkyl aryl sulfonates such as sodium dodecyl benzene sulfonate (sodium lauryl benzene sulfonate)
  v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., C6-30 alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used or a mouthwash are typically on the order of one tenth that used for a toothpaste. In one embodiment, the anionic surfactant is present in a toothpaste at from about 0.3% to about 4.5% by weight, e.g., about 1.5%. The compositions of the invention may optionally contain mixtures of surfactants, e.g., comprising anionic surfactants and other surfactants that may be anionic, cationic, zwitterionic or nonionic. Generally, surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al., which are incorporated herein by reference. In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. In a particular embodiment, the composition of the invention, e.g., Composition 1, et seq., comprises sodium lauryl sulfate.

In another embodiment, cationic surfactants useful in the present invention can be broadly defined as derivatives of aliphatic quaternary ammonium compounds having one long alkyl chain containing about 8 to about 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof. Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants that can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

In certain embodiments, zwitterionic synthetic surfactants useful in the present invention can be broadly described as derivatives of aliphatic quaternary ammonium, phosphomium, and sulfonium compounds, in which the aliphatic radicals can be straight chain or branched, and wherein one of the aliphatic substituents contains about 8 to about 18 carbon atoms and one contains an anionic water-solubilizing group, e.g., carboxy, sulfonate, sulfate, phosphate or phosphonate. Illustrative examples of the surfactants suited for inclusion into the composition include, but are not limited to, sodium alkyl sulfate, sodium lauroyl sarcosinate, cocoamidopropyl betaine and polysorbate 20, and combinations thereof.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

Flavoring Agents:

The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of about 0.1 to about 5% by weight and about 0.5 to about 1.5% by weight. The dosage of flavoring agent in the individual oral care composition dosage (i.e., a single dose) is about 0.001 to about 0.05% by weight and in another embodiment about 0.005 to about 0.015% by weight.

Polymers:

The oral care compositions of the invention also optionally include one or more polymers, such as polyethylene glycols, polyvinylmethyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts.

Particularly when noncationic antibacterial agents or antibacterial agents, e.g., triclosan, are included in any of the dentifrice components, there is also preferably included from about 0.05 to about 5% of an agent which enhances the delivery and retention of the agents to, and retention thereof on oral surfaces. Such agents useful in the present invention are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 300,000 to about 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from about 0.05 to about 3% by weight. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference. Another useful class of polymeric agents includes polyamino acids containing proportions of anionic surface-active amino acids such as aspartic acid, glutamic acid and phosphoserine, (in addition to the basic amino acid polymers), e.g. as disclosed in U.S. Pat. No. 4,866,161 Sikes et al., incorporated herein by reference. In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

Enzymes:

The oral care compositions of the invention may also optionally include one or more enzymes. Useful enzymes include any of the available proteases, glucanohydrolases, endoglycosidases, amylases, mutanases, lipases and mucinases or compatible mixtures thereof. In certain embodiments, the enzyme is a protease, dextranase, endoglycosidase and mutanase. In another embodiment, the enzyme is papain, endoglycosidase or a mixture of dextranase and mutanase. Additional enzymes suitable for use in the present invention are disclosed in U.S. Pat. No. 5,000,939 to Dring et al., U.S. Pat. No. 4,992,420; U.S. Pat. No. 4,355,022; U.S. Pat. No. 4,154,815; U.S. Pat. No. 4,058,595; U.S. Pat. No. 3,991,177; and U.S. Pat. No. 3,696,191 all incorporated herein by reference. An enzyme of a mixture of several compatible enzymes in the current invention constitutes about 0.002% to about 2.0% in one embodiment or about 0.05% to about 1.5% in another embodiment or in yet another embodiment about 0.1% to about 0.5%.

Water:

Water may also be present in the oral compositions of the invention. Water, employed in the preparation of commercial oral compositions should be deionized and free of organic impurities. Water commonly makes up the balance of the compositions and includes about 10% to about 90%, about 20% to about 60% or about 10% to about 30% by weight of the oral compositions. This amount of water includes the free water which is added plus that amount which is introduced with other materials such as with sorbitol or any components of the invention.

Humectants:

Within certain embodiments of the oral compositions, it is also desirable to incorporate a humectant to prevent the composition from hardening upon exposure to air. Certain humectants can also impart desirable sweetness or flavor to dentifrice compositions. The humectant, on a pure humectant basis, generally includes about 15% to about 70% in one embodiment or about 30% to about 65% in another embodiment by weight of the dentifrice composition. Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the toothpaste compositions herein.

Other Optional Ingredients:

In addition to the above-described components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

Example 1 a. Mixed Species Biofilm Test

Mixed species bacteria are grown as follows: *Actinomyces viscosus* (ATCC #31346) is grown in trypticase soy broth supplemented with 0.6% yeast extract (TSB-YE) at 37° C., static culture. For mixed species assays, the source of bacteria is a continuous culture chemostat inoculated with *A. viscosus, Lactobacillus casei* (ATCC #334), *Streptococcus oralis* (ATCC #35037), *Fusobacterium nucleatum* (ATCC #10953), and *Veilonella parvula* (ATCC #17745). This mixed culture is maintained in a specialized complex medium in a continuous culture chemostat at 37° C.

Mixed species biofilms are preformed on saliva-coated HAP disks (scHAP). Following saliva coating, disks are inoculated with 1 ml of mixed species culture from the continuous culture chemostat described above diluted to an OD610 of ~0.2 in 0.5×TSB. Plates are incubated for 48 h at 37° C. to allow biofilms to form.

Disks containing preformed biofilms are transferred to a fresh 24-well culture plate and 1 ml of sterile 0.5×TSB medium containing the indicted concentration of test compound is added to each disk. Plates are incubated for 1 h at 37° C. with gentle agitation. Following treatment, disks are removed to a plate containing fresh 0.5×TSB to rinse off the treatment solution and any loosened biofilm. Disks are then transferred to a plate containing fresh sterile 0.5×TSB and incubated for 24 h to allow the remaining biofilm to regrow, in order to amplify the effects of biofilm removal. Following this regrowth period, disks are then transferred to 15 ml polystyrene tubes containing 1 ml of a 0.25% trypsin solution. Disks are incubated at 37° C. with shaking for 45 min. Tubes are briefly vortexed to resuspend the bacteria and supernatants are transferred to a fresh 24-well plate. Plates are sonicated for 2 min to pellet any residual HAP and supernatants are removed to fresh plates so that absorbance could be read at 610 nm.

All samples are tested in triplicate and the average of the three wells determined. Results are reported as a percent reduction in biofilm formation relative to a disks treated with media alone.

b. Gallium Effect on Biofilms

Gallium nitrate is assessed in oral biofilm models. Gallium nitrate alone has a minimum inhibitory concentration (MIC) of approximately 60 ppm against *Actinomyces viscosus* and, although this is at a level considered antibacterial, it is not a particularly powerful antibacterial agent. Antimicrobial agents currently in use in oral formulations, such as Triclosan, have MTC values less than 10 ppm. The advantage of gallium over other agents is that it appears to target the relatively starved bacteria found deeper in the biofilms that are usually less accessible to traditional antimicrobial agents.

At concentrations as low as 30 ppm, gallium nitrate is able to inhibit the formation of single species *Actinomyces viscosus* biofilms. In a five species biofilm model, 0.05 gallium nitrate incubated with the bacterial inoculum leads to approximately a 20% reduction in biofilm formation on hydroxyapatite (HAP) disks. Similar results are seen for incubation with 0.05% gallium maltoate. In this particular model, triclosan inhibits approximately 55% of biofilm formation.

Thus, while gallium nitrate is effective against single species *Actinomyces viscosus* biofilms, its activity against multiple species biofilms as are found in the oral cavity is much less than the activity of existing commercial antibacterial agents for oral care use.

c. ε-Polylysine Effects on Biofilm

ε-Polylysine is found to have an MIC<1 ppm for *A. viscosus*, but does not have antimicrobial activity against any other oral bacterial species tested. While ε-polylysine is able to inhibit single-species *A. viscosus* biofilms at concentrations<1 ppm, 250 ppm of ε-polylysine provides less than 20% inhibition of multispecies biofilm formation.

d. Effects of Combinations of Gallium and ε-Polylysine

When 250 ppm of ε-polylysine and 250 ppm of gallium nitrate are coincubated with a five species mix of bacteria and biofilms allowed to form on scHAP disks for 48 h, a 46% reduction in biofilm formation relative to media alone is observed. Additionally, when 500 ppm of gallium maltolate is combined with 125-250 ppm of ε-polylysine, a similar inhibition of biofilm formation is observed.

These data demonstrate that although gallium compounds alone have only a minimal effect on multispecies oral biofilms, when used in conjunction with ε-polylysine, they are able to greatly inhibit the formation of oral biofilms in vitro.

The biofilm inhibition observed in these experiments appears to represent more than a simple additive effect of the effects of the two individual compounds. Indeed, the degree of inhibition using the compounds together is far greater than the maximum inhibition of either compound alone. Without being bound by theory, we believe that, although unable to prevent or disrupt multispecies biofilms on its own, the positively charged ε-polylysine could nevertheless compromise the biofilm structure and increase the porosity of the overall biofilm, thereby providing greater access for $Ga^{3+}$ ions to the parts of the biofilm where they are most effective. It is therefore believed that other polymers of basic amino acids, such as polyarginine would also be effective to enhance the effects of the gallium salt.

The invention claimed is:

1. An oral care composition comprising: (i) an orally acceptable gallium salt and (ii) a basic amino acid polymer; wherein the combination of the gallium salt and the basic amino acid polymer is present at a concentration effective to disrupt biofilm and wherein the basic amino acid polymer is ε-polylysine.

2. The composition according to claim 1 wherein the orally acceptable gallium salt is selected from gallium nitrate, gallium citrate, gallium maltolate, and mixtures thereof.

3. The composition according to claim 1 wherein the amount of orally acceptable gallium salt is from 0.001 to 5%.

4. The composition according to claim 1 wherein the amount of basic amino acid polymer is from 0.001 to 5%.

5. The composition according to claim 1 further comprising effective amounts of additional agents selected from fluoride, l-arginine in free or orally acceptable salt form, antibacterial agents in addition to the gallium salt and the basic amino acid polymer, anti-inflammatory compounds, and whitening agents.

6. The composition according to claim 1 in a form selected from mouthrinse, toothpaste, tooth gel, tooth powder, non-abrasive gel, mousse, foam, mouth spray, lozenge, oral tablet, dental implement, and pet care product.

7. The composition according to claim 1 wherein the composition is a toothpaste or mouthwash optionally further comprising one or more of one or more of water, abrasives, surfactants, foaming agents, vitamins, polymers, enzymes, humectants, thickeners, antimicrobial agents, preservatives, flavorings, colorings and/or combinations thereof.

8. The composition according to claim 1, wherein the biofilm is a multispecies biofilm.

9. A method to (i) inhibit microbial biofilm formation in the oral cavity, (ii) reduce plaque accumulation, (iii) reduce or inhibit gingivitis, (iv) reduce levels of acid producing bacteria, and/or (v) promote or maintain whole body health; comprising applying to the oral cavity an effective amount of a composition according to any of the foregoing claims.

10. The composition according to claim 3 wherein the amount of basic amino acid polymer is from 0.001 to 5%.

11. The composition according to claim 10 wherein the orally acceptable gallium salt is selected from gallium nitrate, gallium citrate, gallium maltolate, and mixtures thereof.

12. The composition according to claim 11 wherein the composition is a toothpaste or mouthwash optionally further comprising one or more of one or more of water, abrasives, surfactants, foaming agents, vitamins, polymers, enzymes, humectants, thickeners, antimicrobial agents, preservatives, flavorings, colorings and/or combinations thereof.

* * * * *